US008561607B2

(12) United States Patent
Cortez, Jr. et al.

(10) Patent No.: US 8,561,607 B2
(45) Date of Patent: Oct. 22, 2013

(54) HEATED NEBULIZER DEVICES, NEBULIZER SYSTEMS, AND METHODS FOR INHALATION THERAPY

(75) Inventors: Felino V. Cortez, Jr., Bowie, MD (US); William F. Niland, Arnold, MD (US); Peter Boyd, Charlottesville, VA (US); George McGarrity, Centreville, MD (US); Carl Buyer, Denton, MD (US)

(73) Assignee: Vapotherm, Inc., Stevensville, MD (US)

( * ) Notice: Subject to any disclaimer, the term of this patent is extended or adjusted under 35 U.S.C. 154(b) by 669 days.

(21) Appl. No.: 12/701,116

(22) Filed: Feb. 5, 2010

(65) Prior Publication Data

US 2010/0258114 A1 Oct. 14, 2010

Related U.S. Application Data

(60) Provisional application No. 61/150,368, filed on Feb. 6, 2009, provisional application No. 61/228,304, filed on Jul. 24, 2009, provisional application No. 61/228,308, filed on Jul. 24, 2009.

(51) Int. Cl.
*A61M 15/00* (2006.01)
*A61M 16/10* (2006.01)
*A61M 16/00* (2006.01)
*F24J 3/00* (2006.01)

(52) U.S. Cl.
USPC ............ 128/203.12; 128/200.24; 128/203.26; 128/204.17

(58) Field of Classification Search
USPC .......................... 128/200.14, 200.18, 200.24, 128/203.12–203.17
See application file for complete search history.

(56) References Cited

U.S. PATENT DOCUMENTS

| | | | | |
|---|---|---|---|---|
| 3,864,326 | A * | 2/1975 | Babington | 261/142 |
| 4,177,945 | A * | 12/1979 | Schwartz et al. | 239/338 |
| 4,819,625 | A | 4/1989 | Howe | |
| 4,832,012 | A * | 5/1989 | Raabe et al. | 128/200.21 |
| 4,911,157 | A | 3/1990 | Miller | |
| 5,226,411 | A | 7/1993 | Levine | |
| 5,461,695 | A | 10/1995 | Knoch | |
| 5,630,409 | A | 5/1997 | Bono et al. | |
| 2004/0237178 | A1 | 12/2004 | Landeros | |
| 2008/0000470 | A1 * | 1/2008 | Minocchieri et al. | 128/200.21 |

FOREIGN PATENT DOCUMENTS

RU 2009111135 A 10/2010

OTHER PUBLICATIONS

International Search Report, dated Oct. 18, 2010.
International Search Report dated Apr. 21, 2013, application No. PCT/US2013/022692.

* cited by examiner

*Primary Examiner* — Nicholas Lucchesi
*Assistant Examiner* — Leah Stohr
(74) *Attorney, Agent, or Firm* — RatnerPrestia

(57) ABSTRACT

Nebulizer assemblies and systems are disclosed. A nebulizer assembly includes a reservoir and a nebulizer for producing an aerosolized gas. An aerosolized gas outlet passes the aerosolized gas. A breathing gas mixing chamber is coupled to an outlet port of the nebulizer to entrain nebulized medication into a breathing gas. A system and method of heating medication in a reservoir and adding medication to a gas flow is also provided.

20 Claims, 18 Drawing Sheets

```
                    ┌─────────────────────────┐
                    │  OPERATE NEBULIZER 101 TO│
                    │    NEBULIZE MEDICATION  │──1302
                    │     ACCORDING TO THE    │
                    │  OPERATION OF NEBULIZER 101│
                    └─────────────────────────┘
```

1300

1306

```
     ┌─────────────────────┐        ┌─────────────────────┐
     │  TRANSMIT NEBULIZED │──1304  │  TRANSMIT GAS FROM  │
     │    MEDICATION INTO  │        │     INLET 116 AND   │
     │  MIXING CHAMBER 115 │        │    ACROSS GAP 122   │
     └─────────────────────┘        │   AND TO OUTLET 118 │
                                    └─────────────────────┘
```

1308
```
     ┌─────────────────────────────┐        ┌─────────────────────┐
     │   THE GAS FLOW DRAWS THE    │   1312 │  COLLECT NEBULIZED  │
     │   NEBULIZED MEDICATION INTO │        │   MEDICATION THAT   │
     │    GAP 122 AND TO OUTLET 118│        │   IS NOT DRAWN INTO │
     │   FOR MIXING WITH THE GAS FLOW│      │   GAP 122 IN DRAIN  │
     └─────────────────────────────┘        │    COLLECTOR 220    │
                                            └─────────────────────┘
```

1310
```
     ┌─────────────────────────────┐
     │  TRANSMIT THE GAS FLOW WITH │
     │    THE NEBULIZED MEDICATION │
     │    TO A BREATHING DEVICE FOR│
     │    INHALATION BY THE PATIENT│
     └─────────────────────────────┘
                    │
                  ( END )
```

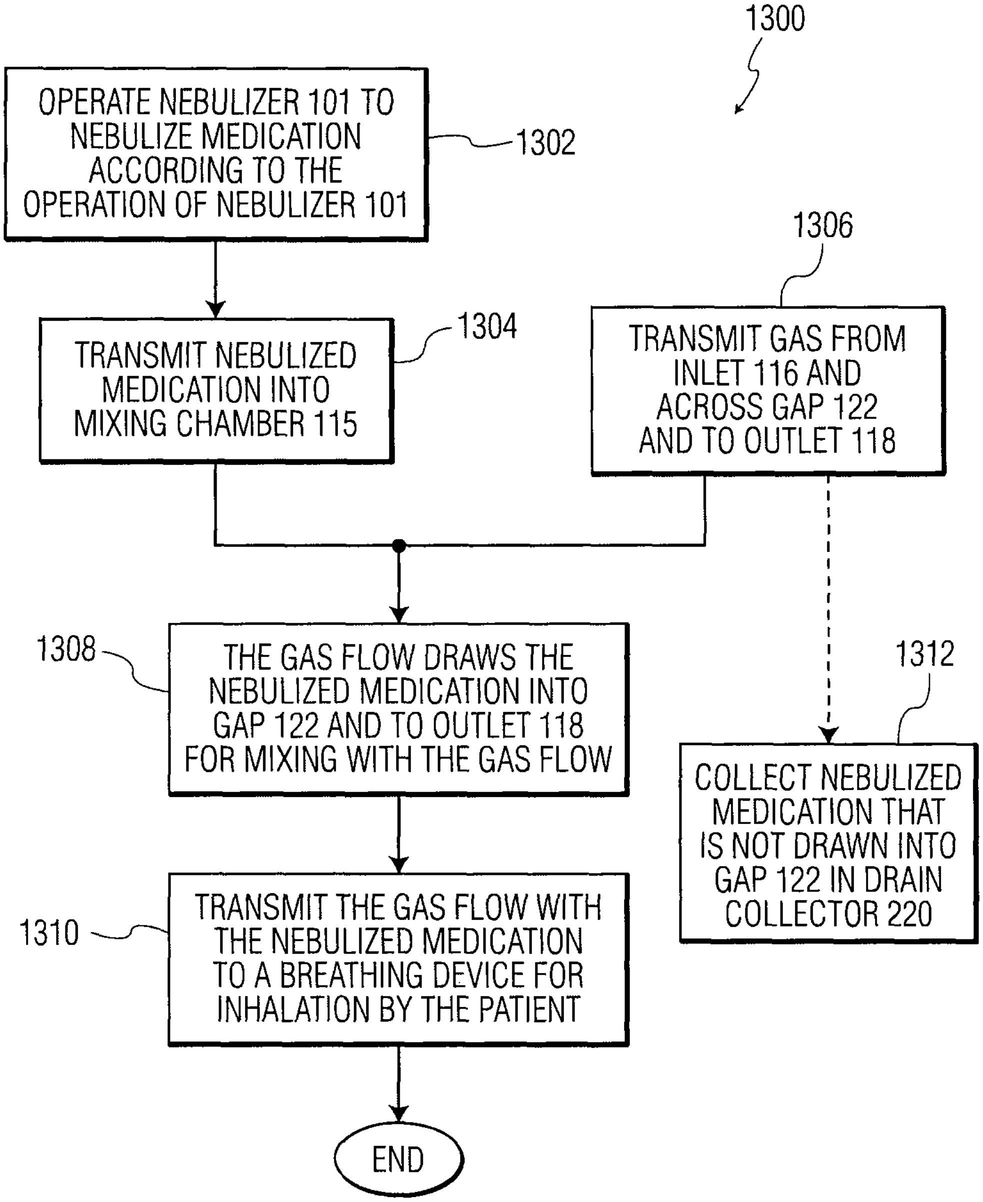

FIG. 13

HEATED NEBULIZER DEVICES, NEBULIZER SYSTEMS, AND METHODS FOR INHALATION THERAPY

CROSS-REFERENCE TO RELATED APPLICATION

The present application claims the benefit of U.S. Patent Application No. 61/150,368, entitled "HEATED NEBULIZER DEVICE FOR ADDING AEROSOLIZED MEDICAMENT TO A BREATHING GAS" filed on 6 Feb. 2009, U.S. Patent Application No. 61/228,304, entitled "NEBULIZER SYSTEMS AND METHODS FOR INHALATION THERAPY" filed on 24 Jul. 2009, and U.S. Patent Application No. 61/228,308, entitled "NEBULIZER FOR ACCELERATED AEROSOL DELIVERY WITH FLOW CONTROL" filed on 24 Jul. 2009, all of which are incorporated herein by reference in their entireties.

BACKGROUND OF THE INVENTION

Patients with respiratory ailments may be administered supplemental breathing gases, such as oxygen, for example, to aid in respiration. These breathing gases may be provided from a breathing gas supply, such as an oxygen tank. A delivery device, such as a nasal cannula, may be coupled to the breathing gas supply and inserted into a patient's nasal passages for delivery of the breathing gas to the patient for inhalation.

Separately, respiratory medications may be administered through inhalation directly to the patient's lungs. These respiratory medications may be aerosolized by a nebulizer in order to generate small particles of the medication, which facilitate distribution throughout the patient's lungs during inhalation.

Nebulizers produce a fine mist for inhalation by a patient. The mist may include a medicament for delivery to the respiratory tract of the patient. A conventional nebulizer uses pressurized air to form a gas jet that creates a venturi vacuum to draw liquid medicament from a liquid reservoir to form a nebulized aerosol for inhalation.

SUMMARY OF THE INVENTION

Aspects of the present invention are directed to nebulizer assemblies, nebulizer systems, nebulizer adaptors, and methods for adding medication to a gas flow for inhalation.

In accordance with one aspect of the present invention, a nebulizer assembly includes a reservoir for containing a liquid, a nebulizer for producing an aerosolized gas using the liquid, an aerosolized gas outlet, and a heating chamber. The aerosolized gas outlet is coupled to the nebulizer to pass the aerosolized gas. The heating chamber is disposed around an exterior of the reservoir. The heating chamber includes a heating fluid inlet in fluid communication with the heating chamber for providing heating fluid to the heating chamber and a heating fluid outlet in fluid communication with the heating chamber for discharging the heating fluid from the heating chamber.

In accordance with another aspect of the present invention, a method of heating a medication to be nebulized and providing the nebulized medication to a patient for inhalation includes generating a heated and humidified breathing gas, transmitting the heated and humidified breathing gas through a first lumen in a delivery tube, insulating the heated and humidified breathing gas with a fluid flowing through a second lumen in the delivery tube, discharging the heated and humidified breathing gas from the delivery tube to a chamber, providing a medication in a nebulizer reservoir, transmitting the fluid from the second lumen to a heating cavity surrounding the nebulizer reservoir; thereby heating the medication in the nebulizer reservoir with the fluid, nebulizing the medication in the nebulizer reservoir, combining the nebulized medication with the heated and humidified breathing gas in the chamber, and transmitting the combined nebulized medication and heated and humidified breathing gas to a patient for inhalation.

In accordance with yet another aspect of the present invention, a nebulizer system includes a nebulizer for generating an aerosol mist of a medication, and a breathing gas mixing chamber. The nebulizer includes a nebulizer outlet port. The breathing gas mixing chamber is coupled to the nebulizer outlet port. The breathing gas mixing chamber includes a nebulizer coupling port, a breathing gas inlet, a breathing gas outlet, and an opening between the breathing gas inlet and the breathing gas outlet. The nebulizer coupling port is in fluid communication with the nebulizer outlet port. The breathing gas inlet is adapted to couple to a gas delivery system. The breathing gas outlet is adapted to couple to a breathing device. The opening is in fluid communication with the nebulizer outlet port.

In accordance with still another aspect of the present invention, a method of adding a medication to a gas flow includes nebulizing the medication and entraining the nebulized medication into the gas flow.

In accordance with another aspect of the present invention, a nebulizer adaptor for entraining a nebulized medication into a breathing gas includes a mixing chamber, a nebulizer coupling port, a breathing gas inlet, a breathing gas outlet, and an opening between the breathing gas inlet and the breathing gas outlet. The nebulizer coupling port is adapted to coupled to a nebulizer outlet port. The breathing gas inlet is adapted to couple to a gas delivery system. The breathing gas outlet is adapted to couple to a breathing device. The opening is in fluid communication with the nebulizer coupling port.

BRIEF DESCRIPTION OF THE DRAWINGS

The foregoing summary, as well as the following detailed description of preferred embodiment of the inventions, will be better understood when read in conjunction with the appended drawings, which are incorporated herein and constitute part of this specification. For purposes of illustrating the invention, there are shown in the drawings an exemplary embodiment of the present invention. It should be understood, however, that the invention is not limited to the precise arrangements and instrumentalities shown. In the drawings, the same reference numerals, are employed for designating the same elements throughout the several figures. In the drawings:

FIG. 13 is a flow chart illustrating operation of exemplary embodiments of the inventive nebulizer assembly;

DETAILED DESCRIPTION OF THE INVENTION

Certain terminology is used herein for convenience only and is not to be taken as a limitation on the present invention. The terminology includes the words specifically mentioned, derivatives thereof and words of similar import. The following describes exemplary embodiments of the invention. It should be understood based on this disclosure, however, that the invention is not limited by the exemplary embodiments of the invention.

Embodiments of the present invention provide a heated nebulizer assembly 100 configured for delivering aerosolized medicament in a heated and humidified breathing gas for inhalation. The aerosolized medicament includes medication in very small particles, e.g., 0.5-1.5 microns in average diameter, allowing the medicament to reach the user's lungs in an efficient manner. Nebulizer assembly 100 is heated in order to warm the medicament prior to the medicament being nebulized so as not to adversely lower the temperature of the heated and humidified breathing gas into which the nebulized medication is mixed prior to inhalation by the user.

Figure 1:
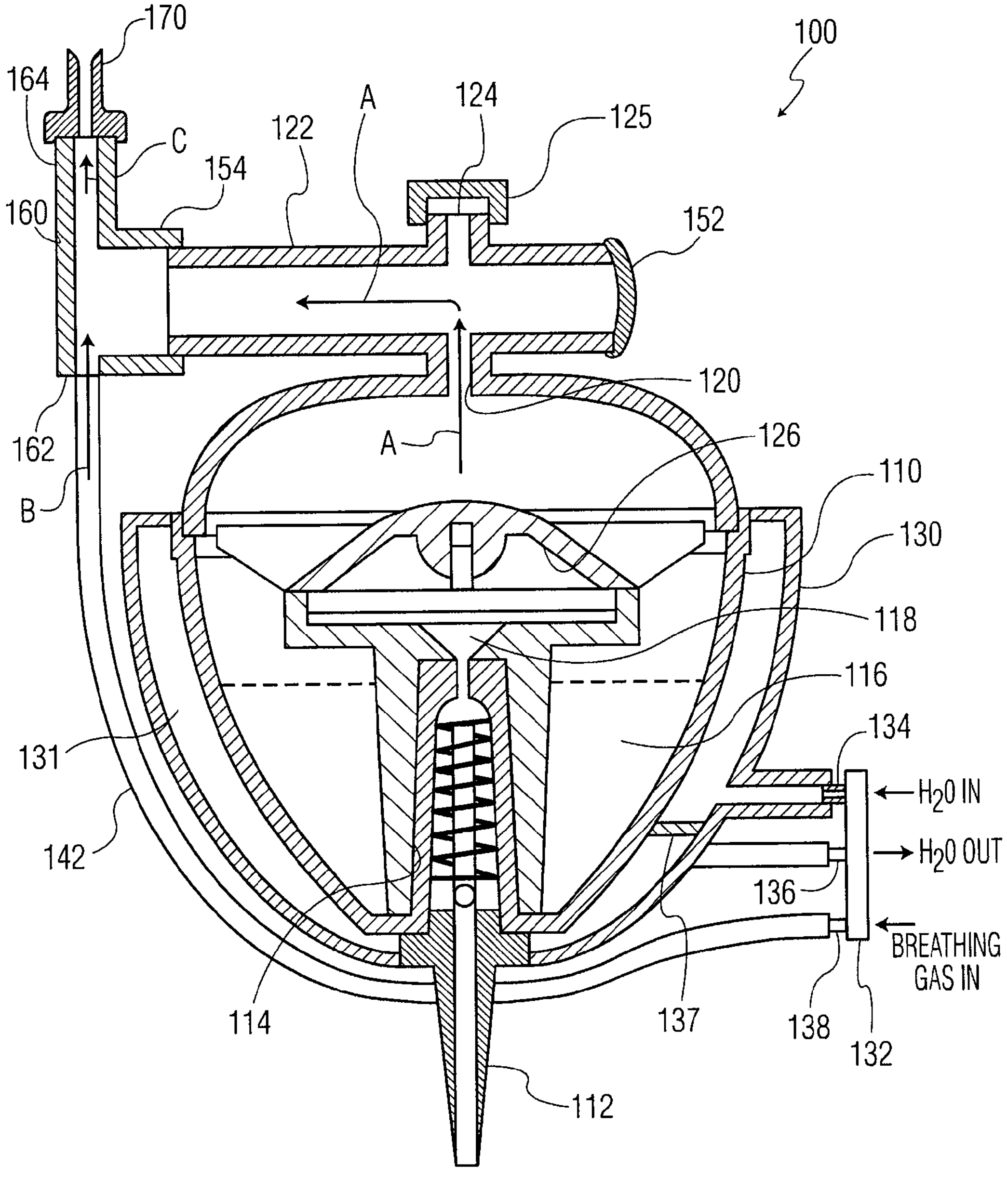
FIG. 1 is a front perspective view, partially cut away, of an exemplary embodiment of a heated nebulizer assembly according to the present invention.
Figure 2:
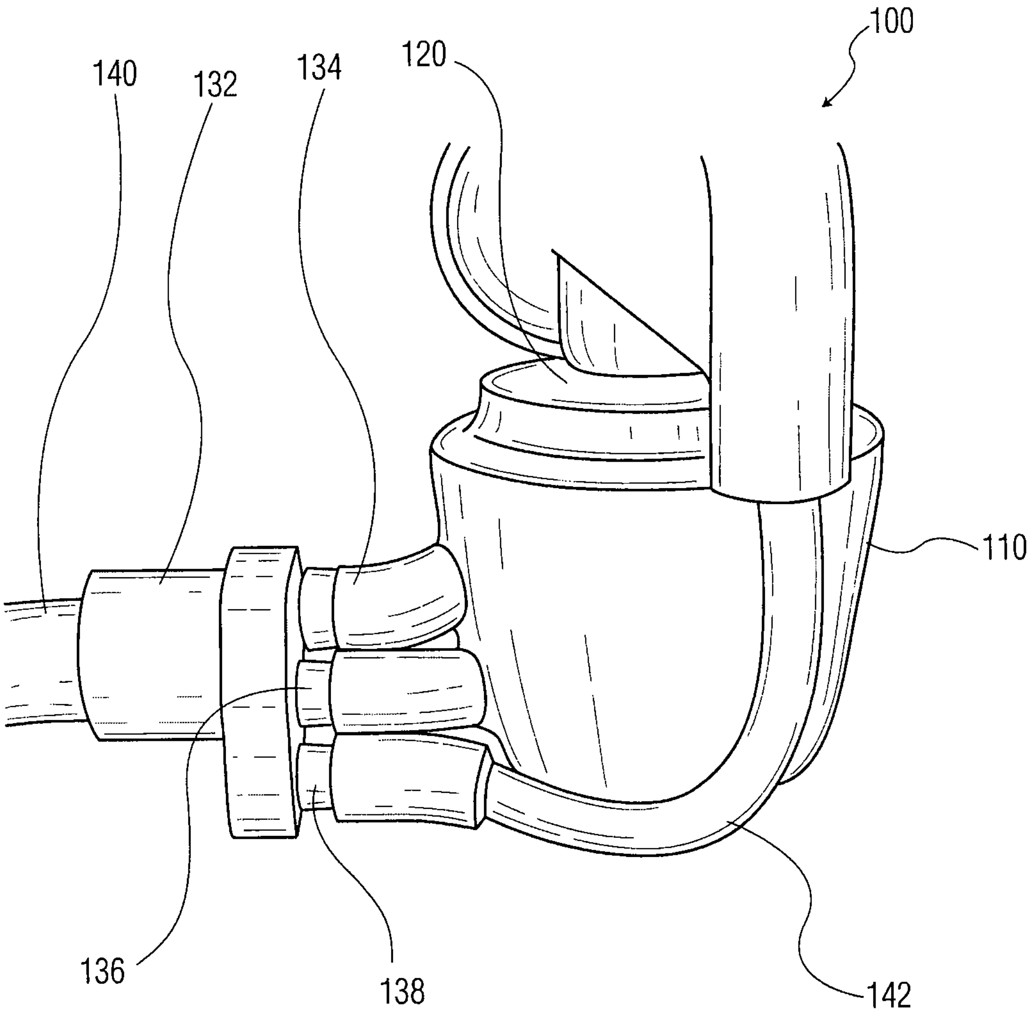
FIG. 2 is a rear perspective view of the heated nebulizer assembly of FIG. 1.

Referring to FIGS. 1 and 2, nebulizer assembly 100 includes a nebulizer 110 that entrains medication in an air flow to generate an aerosolized mist for inhalation by a patient. Nebulizer 110 includes an inlet 112 that provides a connection to a supply of air (not shown), such as, for example, a high pressure air supply of between about 35 and about 50 psi, with a flow rate of less than about 10 liters per minute, and desirably, about 6 liters per minute. The supplied air in the illustrated embodiment flows through an air swirler 114 to a nebulizing chamber 118. It is contemplated that air swirler 114 may be omitted in alternative embodiments of the present invention.

Medication is contained in a reservoir 116 (e.g., in liquid form; i.e., a liquid medicament) and is aerosolized in nebulizing chamber 118 by the supplied air to form an aerosol. The aerosol exits nebulizer 110 through discharge port 120 in the direction of arrow "A" (shown in FIG. 4) to an outlet tube 122. A fill port 124 in outlet tube 122 may be used to add medication to reservoir 116. A cap 125 is releasably coupled to fill port 124. Cap 125 may be removed from fill port 124 to add medication to reservoir 116 and then replaced over fill port 124 after the medication has been added to reservoir 116. As the medication is poured into nebulizer 110 through fill port 124, a deflector 126 deflects the medication away from nebulizing chamber 118 and to reservoir 116.

A design of an exemplary nebulizer that may be modified for use as nebulizer 110 is described in U.S. Pat. No. 5,630,409, which is incorporated by reference herein in its entirety. While the nebulizer 110 described in this reference may use a pressurized air supply, other types of nebulizers may alternatively be used. Such nebulizers may include a jet nebulizer, also known as a small-volume nebulizer (SVN). In an exemplary embodiment, one of three types of SVNs are used. A first type of SVN is a pneumatic nebulizer. Pneumatic nebulizers use a pressurized gas stream to draw fluid out of a fluid reservoir and shear the fluid into small particles. Many of the medicaments that are delivered through these nebulizers are used to treat common lung conditions, such as asthma and Chronic Obstructive Pulmonary Disease (COPD).

A second type of SVN is a vented nebulizer. Vented nebulizers make aerosol from pneumatic sources and feature a venting system. When the patient breathes in, he/she inhales a richer mix of aerosol, and when the user exhales, he/she does so through an expiratory valve in the mouthpiece so he/she continues to collect some aerosol in the nebulizer.

A third type of SVN is a breath-actuated device. Breath-actuated devices produce aerosol when the patient inhales and do not produce aerosol when the patient exhales. Because the drug is not constantly being aerosolized, delivery is more efficient and less of the drug is wasted.

Other types of suitable nebulizers for use with the present invention include, by way of non-limiting example, ultrasonic nebulizers that create aerosol using sound waves generated by a vibrating piezo crystal and vibrating mesh nebulizers that are able to generate high overall output respirable fractions. The nebulizers reduce the amount of drug that is wasted by vibrating a mesh or plate with multiple apertures, which aerosolizes virtually all of the drug solution. The vibrating mesh may be active, where the mesh is vibrated directly and acts as an electronic micropump, or passive, where an ultrasonic horn pushes medication through a mesh.

According to one aspect of the invention, a heating chamber 130 surrounds medicament reservoir 116 regardless of the type of nebulizer used in the nebulizer assembly 100. The illustrated heating chamber 130 defines a cavity 131 with the outside wall of nebulizer 110 that is in fluid communication with a fluid manifold 132. Fluid manifold 132 includes a fluid inlet 134 that provides a supply of heated fluid to cavity 131, and a fluid outlet 136 that discharges the heated fluid from cavity 131. Optionally, as shown in FIG. 1, a baffle 137 may be located in cavity 131 between fluid inlet 134 and fluid outlet 136 to direct the heated fluid from fluid inlet 134, around the periphery of nebulizer 110, prior to being discharged from fluid outlet 136. Fluid manifold 132 also includes a breathing gas supply 138 that provides heated and humidified breathing gas to a user.

Figure 2A:
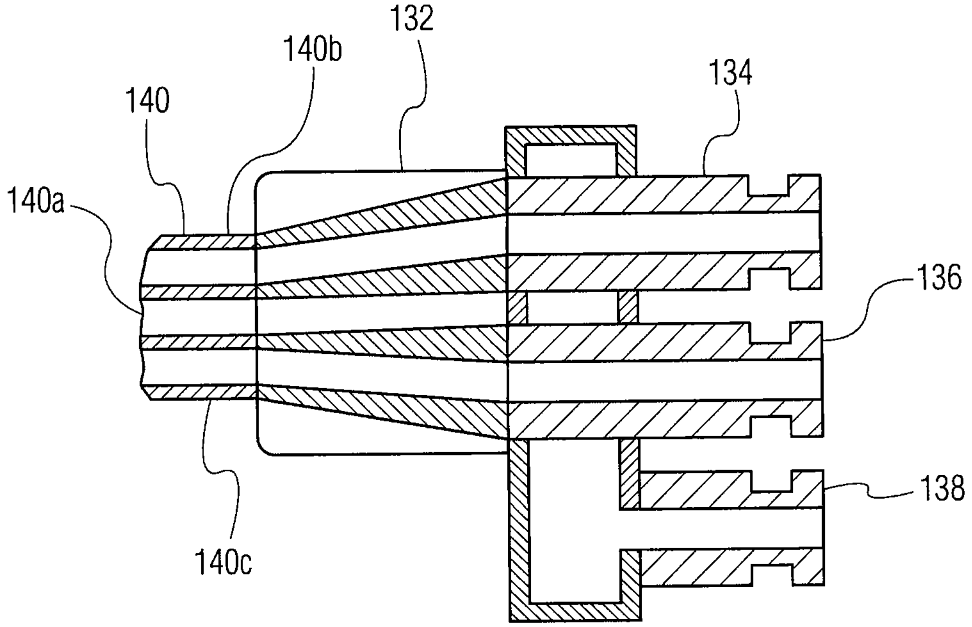
FIG. 2A is a sectional view of a manifold and delivery tube shown in the heated nebulizer assembly of FIG. 2.

Referring to FIG. 2A, fluid manifold 132 is coupled to a delivery tube 140, such as, for example, the delivery tube disclosed in U.S. Pat. No. 7,314,046, which is incorporated herein by reference in its entirety. Delivery tube 140 provides heated and humidified breathing gas in a first lumen 140*a* that is coupled to breathing gas supply 138 in manifold 132. Delivery tube 140 also provides heated fluid via a second lumen 140*b* that is coupled to fluid inlet 134 and heated fluid return via a third lumen 104*c* that is coupled to fluid outlet 136. In an exemplary embodiment, the second and third lumens 140*b*, 140*c*, respectively, surround the first lumen 140*a* such that the heated fluid flowing through the second and third lumens 140*b*, 140*c*, respectively, insulates the heated and humidified breathing gas in the first lumen 140*a*. Fluid manifold 132 enables fluid that is used to insulate the heated and humidified breathing gas as the breathing gas flows through delivery tube 140 to also be used to surround and heat heating chamber 130, as well as the medicament in nebulizer reservoir 116. While a fluid that is used to insulate the heated and humidified breathing gas delivery tube 140 and to also surround and heat the heating chamber 130 may be a liquid, those skilled in the art will recognize that the fluid may be a heated gas instead.

Figure 3:
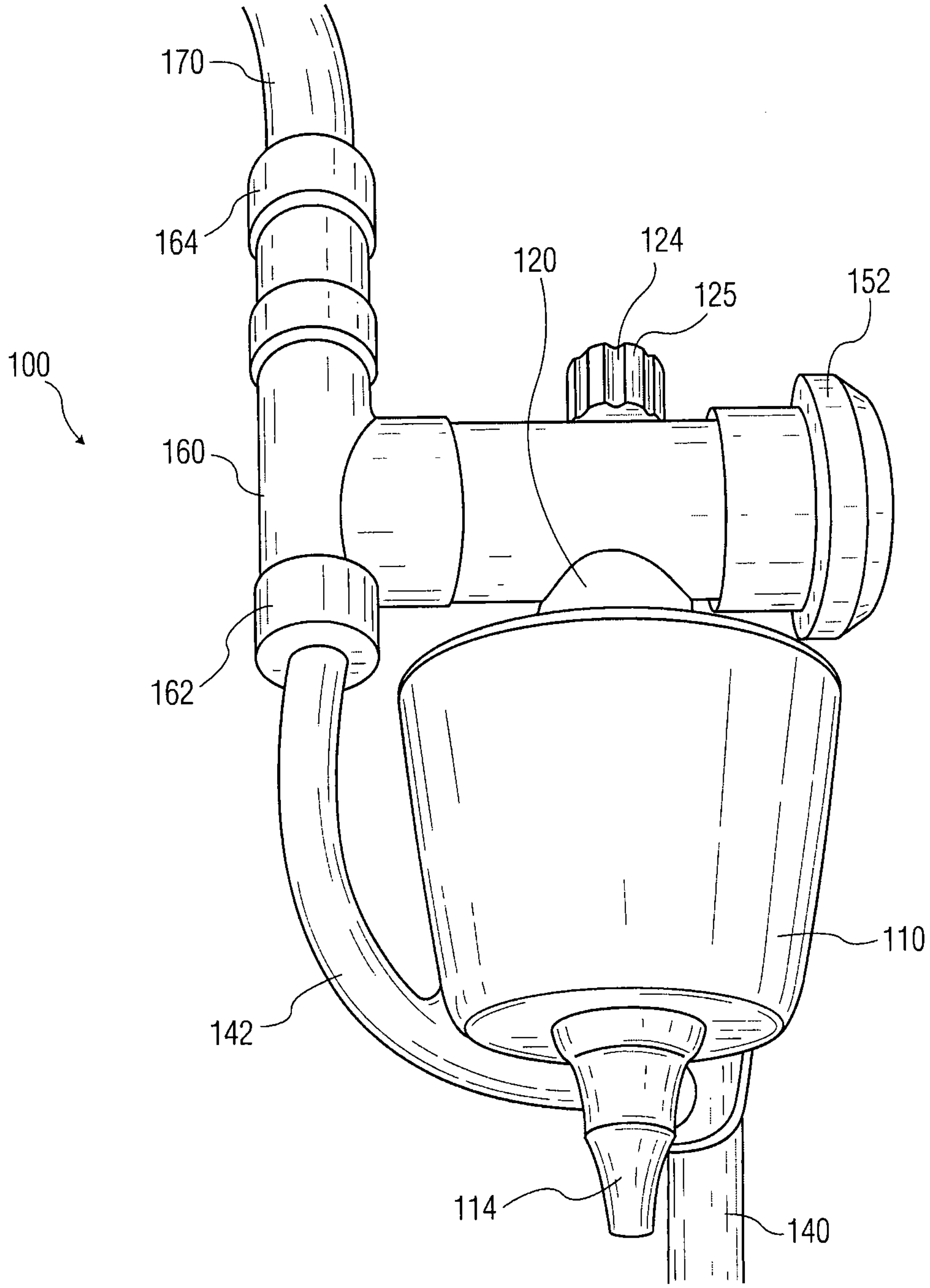
FIG. 3 is a right side perspective view of the heated nebulizer assembly shown in FIG. 1, coupled to a nasal cannula.
Figure 4:
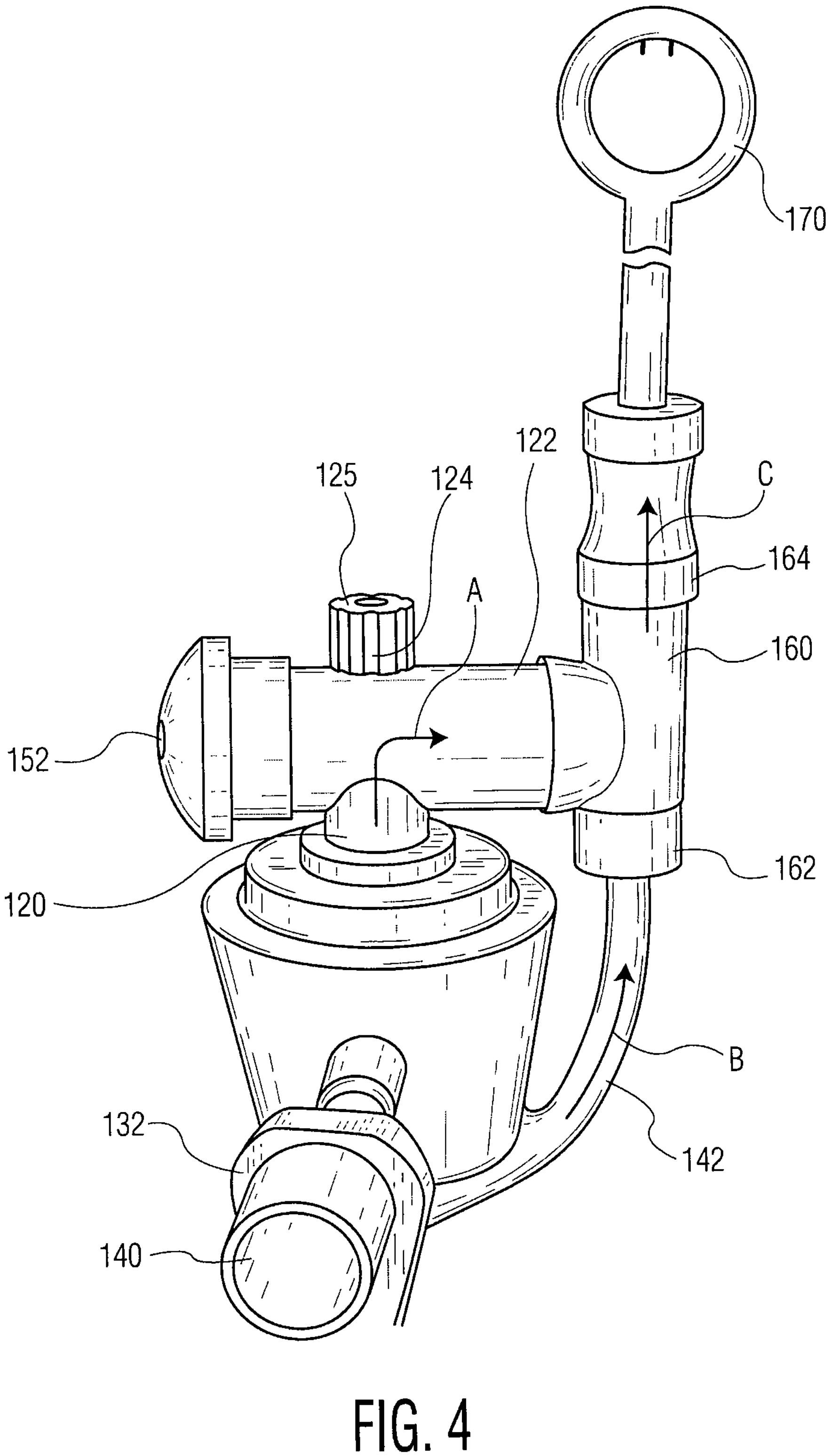
FIG. 4 is a left side perspective view of the heated nebulizer assembly of FIG. 1, coupled to a nasal cannula.

Referring to FIGS. 2-4, breathing gas supply 138 is coupled to a breathing gas conduit 142 that is in fluid communication with discharge port 120 through outlet tube 122. Breathing gas flows in the direction of arrow "B" (shown in FIG. 4). One end of outlet tube 122 includes a relief valve 152 that relieves overpressurization in outlet tube 122. An opposing end of outlet tube 122 is coupled to a chamber, such as a breathing gas flow tee 160, forming a junction between nebulized gas and breathing gas. Breathing gas flow tee 160 includes a first end 162 that is coupled to breathing gas conduit 142 and a second end 164 that is coupled to a nasal cannula 170.

Figure 5:
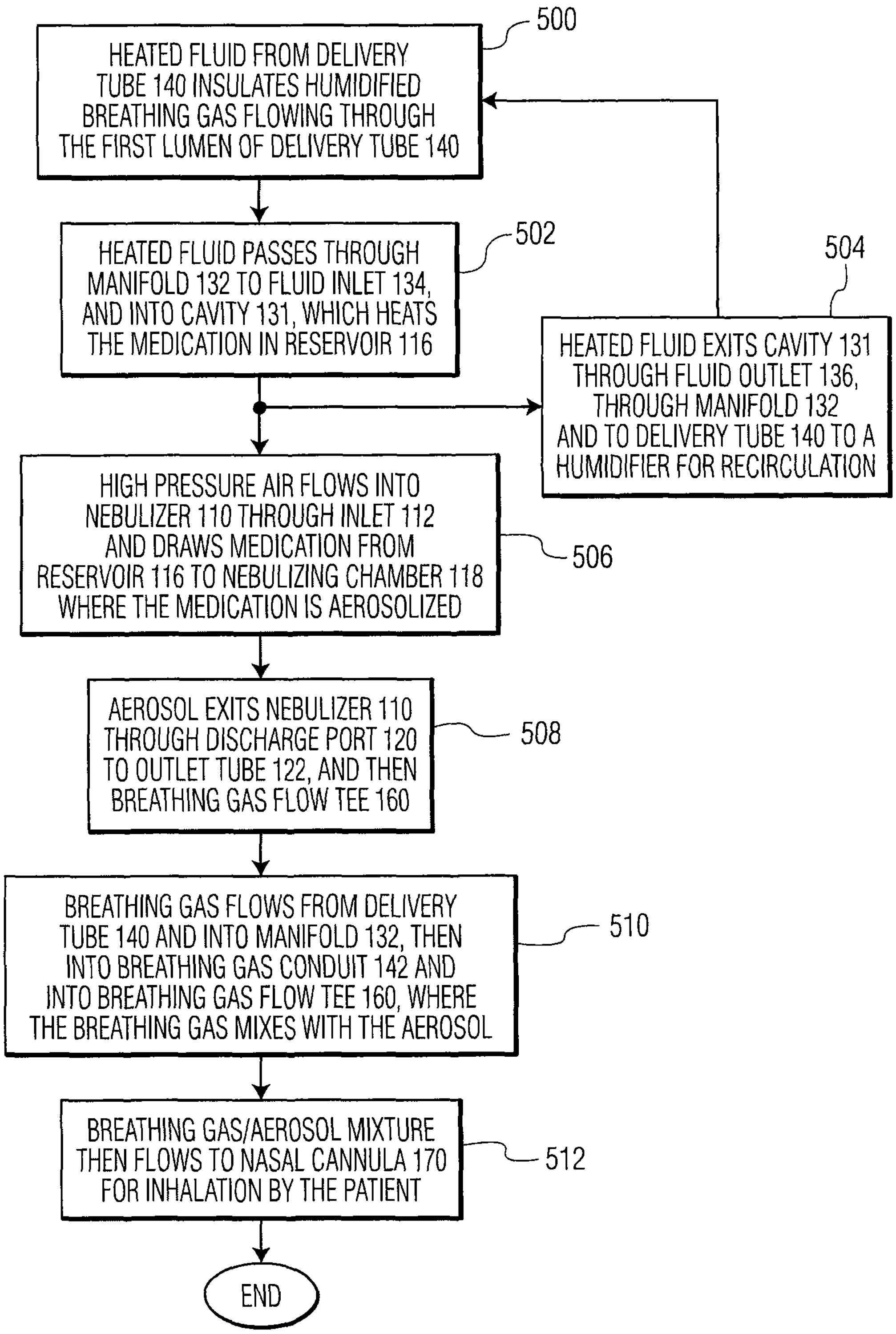
FIG. 5 is a flow chart illustrating steps performed to operate the heated nebulizer assembly of FIGS. 1-4.

Referring to FIG. 5, a flowchart is illustrated showing an exemplary method for heating a medication to be nebulized and providing the nebulized medication to a patient for inhalation. It will be understood by one of ordinary skill in the art that, prior to the steps shown in FIG. 5, a heated and/or humidified breathing gas may be generated by any known means.

In STEP 500, heated fluid in the second and third lumens of delivery tube 140 insulates a heated and humidified breathing gas flowing through first lumen 140*a* of delivery tube 140. The heated fluid flowing through second lumen 140*b* of delivery tube 140 may have a temperature of about 43 degrees Celsius when it reaches manifold 130. In STEP 502, the heated fluid from second lumen 140*b* passes through manifold 132 to fluid inlet 134, and into cavity 131, which heats the medication in reservoir 116. In STEP 504, the heated fluid then exits cavity 131 through fluid outlet 136, which flows through manifold 132 to third lumen 140*c* of delivery tube 140 for recirculation by, for example, a heater of a humidifier (not shown).

In STEP 506, high pressure air flows into nebulizer 110 through inlet 112 and, due to a venturi effect, draws medication from reservoir 116 to nebulizing chamber 118 where the medication is aerosolized. In STEP 508, the aerosol exits nebulizer 110 through discharge port 120 to outlet tube 122, and then to a chamber, such as breathing gas flow tee 160.

In STEP 510, the breathing gas flows from first lumen 140*a* of delivery tube 140, into manifold 132, and then into breathing gas conduit 142 and into a chamber, such as breathing gas flow tee 160, where the breathing gas mixes with the aerosol. The breathing gas flows at a rate of about 10 liters per minute. In STEP 512, the breathing gas/aerosol mixture then flows to nasal cannula 170 in the direction of arrow "C" (shown in FIG. 4) for inhalation by the patient. The breathing gas/aerosol mixture may have a temperature of about 37 degrees Celsius at the output of nasal cannula 170 to a user (not shown).

Embodiments of the present invention are also directed to a device for providing a nebulized aerosol gas therapy to a patient delivered via a breathing device, such as a nasal cannula. In an exemplary embodiment, a breathing gas is warmed and humidified for combination with a nebulized aerosol for delivery at a high flow rate. The combined therapy of warm nebulized medication and high flow therapy for patients experiencing stressful respiratory episodes in acute respiratory compromise may provide a comfortable and effective technique in decreasing bronchial responsiveness while maintaining delivery of high $FiO_2$ to improve oxygen saturation level and decrease work of breathing.

Figure 6:
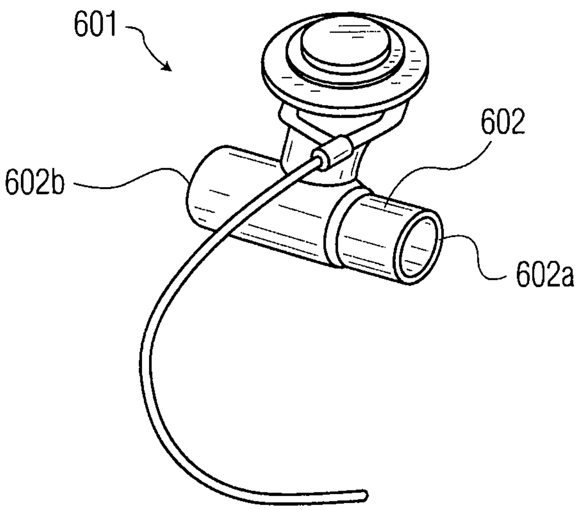
FIG. 6 is a perspective view of a prior art nebulizer system.

An exemplary nebulizer that may be adapted for use with the present invention may be the Aeroneb® Professional nebulizer 601, shown in FIG. 6, available from Aerogen, Ltd of Galway, Ireland. Nebulizer 601 includes an aerosol generator (not shown) that aerosolizes medication contained within nebulizer 601. Typically, less than about 10 ml of medication is used with nebulizer 601. Nebulizer 601 also includes a nebulizer inhalation tube 602 into which nebulized medication flows for inhalation by a user. Inhalation tube 602 includes an inlet end 602*a* that is open to atmosphere during use and an outlet end 602*b* that is inserted into the user's mouth during use.

During use, the user inserts end 602*b* of nebulizer inhalation tube 602 into his/her mouth and inhales. As the user inhales, air from the atmosphere flows through end 602*b* and into nebulizer inhalation tube 602. The inhaled air, with the aerosolized medication entrained therein, then flows through end 602*b*, and into the user's mouth. Other types of nebulizers suitable for use with the present invention will be understood by one of skill in the art from the description herein.

Figure 7:
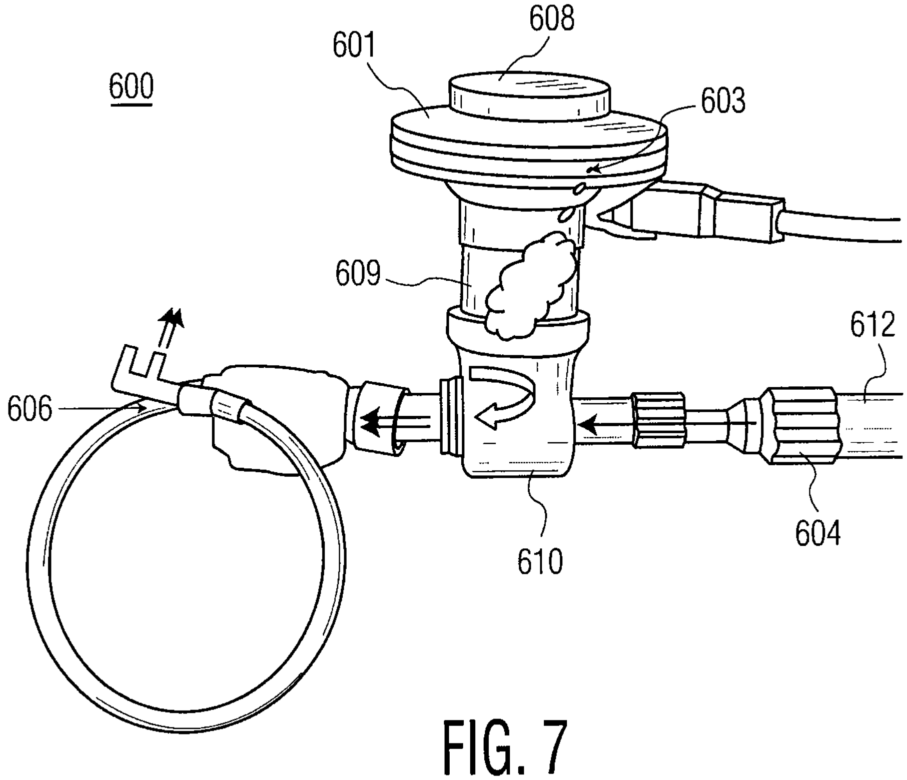
FIG. 7 is a side elevational view of a nebulizer system according to a first exemplary embodiment of the present invention.

Referring to FIGS. 6 and 7, exemplary prior art nebulizer 601 operates using an electrical signal to draw fluid into a vibratory aerosolization element (not shown), to produce an aerosol mist of a medication in the form of a low velocity nebulized aerosol cloud 603. In accordance with an aspect of the present invention, nebulizer 601 may be combined with a high flow heated and humidified gas delivery system 604 to provide a warmed and humidified nebulized aerosol high flow therapy for delivery via a breathing device, such as a nasal cannula 606. In accordance with this aspect, nebulized medication produced by the nebulizer 601 is entrained within a breathing gas flow as the breathing gas flow (which may be heated and humidified) flows past an outlet port 609 of nebulizer 601.

Nebulizer 601 includes a filler cap 608 at the top of nebulizer 601 and an outlet port 609 at the bottom of nebulizer 601. Filler cap 608 may be removed to add liquid medication to nebulizer 601 prior to use.

As shown in FIG. 7, a nebulizer system 600 according to an exemplary embodiment of the present invention may include a T-adapter 610 that connects nebulizer 601 to delivery system 604. In the exemplary embodiment, nebulizer inhalation tube 602 has been removed from nebulizer 601 and replaced with T-adapter 610.

Delivery system 604 may include a delivery tube 612, such as, for example, a delivery tube disclosed in U.S. Pat. No. 7,314,046, which is incorporated fully herein by reference, connected to a supply end of a breathing gas supply (not shown). T-adapter 610 may also connect to nasal cannula 606, providing for fluid communication between delivery system 604 and nasal cannula 606.

Figure 8:
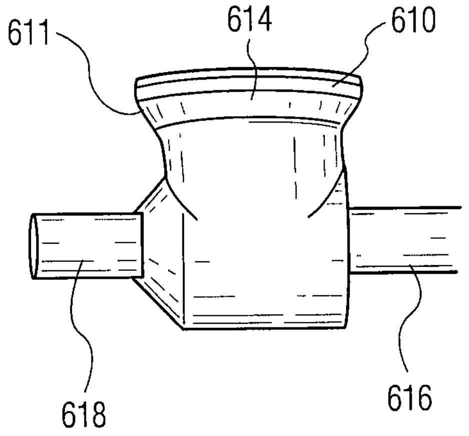
FIG. 8 is a front perspective view of a T-adapter according to an exemplary embodiment of the present invention, for use with the nebulizer system of FIG. 7.
Figure 9:
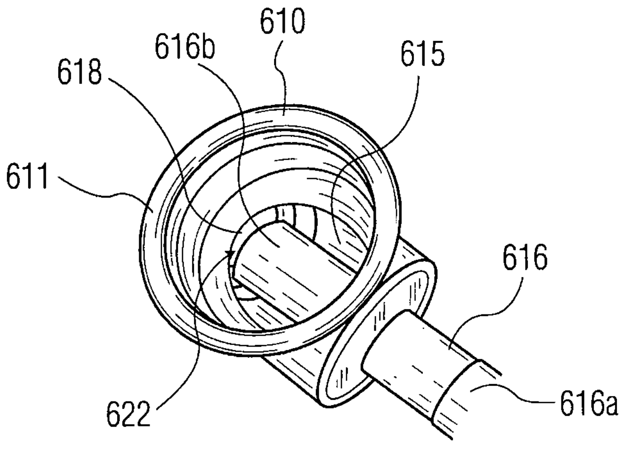
FIG. 9 is a top perspective view of the T-adapter of FIG. 8.

Referring to FIGS. 8 and 9, T-adapter 610 includes a body 611 defining an internal breathing gas mixing chamber 615. T-adapter 610 includes a nebulizer coupling port 614 that couples T-adapter 610 to nebulizer 601. Nebulizer coupling port 614 provides for fluid communication between nebulizer outlet port 609 and internal breathing gas mixing chamber 615 such that aerosolized medication may be transmitted from nebulizer 601 to internal breathing gas mixing chamber 615.

Figure 9A:
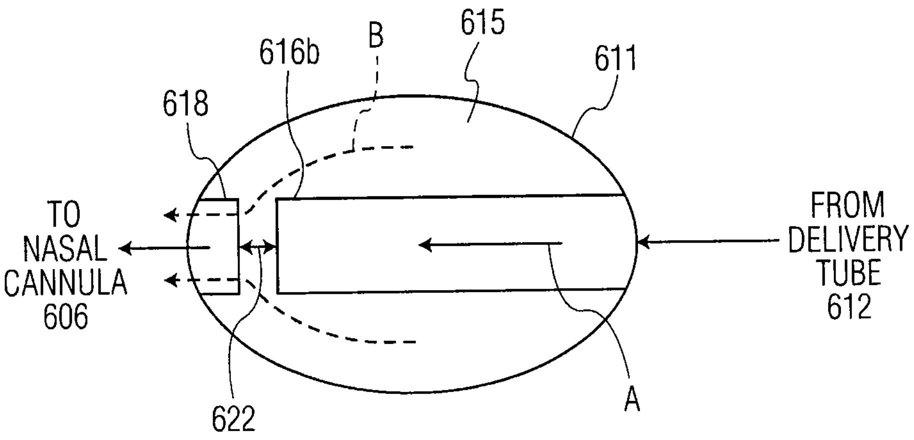
FIG. 9A is a schematic enlarged view of an internal breathing gas mixing chamber of the T-adapter of FIG. 8.

T-adapter 610 also includes a breathing gas inlet 616 having a first end **616*a* extending from body 611 and a second end 616*b* extending through breathing gas mixing chamber 615 of T-adapter 610, terminating within breathing gas mixing chamber 615 between second end 616*b* of breathing gas inlet 616 and a breathing gas outlet 618. Outlet 618 extends outwardly from body 611 and is adapted to couple to a breathing device, such as nasal cannula 606 (shown in FIG. 7). First end 616*a* extends from body 611 and is adapted to couple to gas delivery system 604 (shown in FIG. 7). Inlet 616 and outlet 618 are generally co-axial, with an opening, such as a small gap 622 of about 5 millimeters or less (e.g., about 2 millimeters) separating second end 616*b* of inlet 616 from outlet 618. A schematic view of internal chamber 615 showing gap 622 is shown in FIG. 9A. Solid arrows "A" illustrate the flow of breathing gas through chamber 615 from delivery tube 612, and broken arrows "B" illustrate the flow of aerosolized medication through chamber 615 from nebulizer 601**.

In use, referring to FIGS. 7-9A, aerosol cloud 603 is generated by nebulizer 601 and flows into internal chamber 615 of T-adapter 610. Breathing gas flows from heated and humidified gas delivery system 604 and into inlet 616. In an exemplary embodiment, the breathing gas has a high flow rate, e.g., greater than about one (1) liter per minute for neonatal patients and up to 40 liters per minute in adult patients. The breathing gas exits inlet 616 from second end **616*b*, crosses gap 622, and flows through outlet 618**.

Aerosol cloud 603 is drawn through gap 622 and into outlet 618 by a Venturi effect generated by a flow of gas across gap 622, and into outlet 618, thereby entraining the aerosol into the gas flow. The aerosol cloud 603 combines with the gas and exits through outlet 618 for delivery to the patient via nasal cannula 606.

Figure 10:
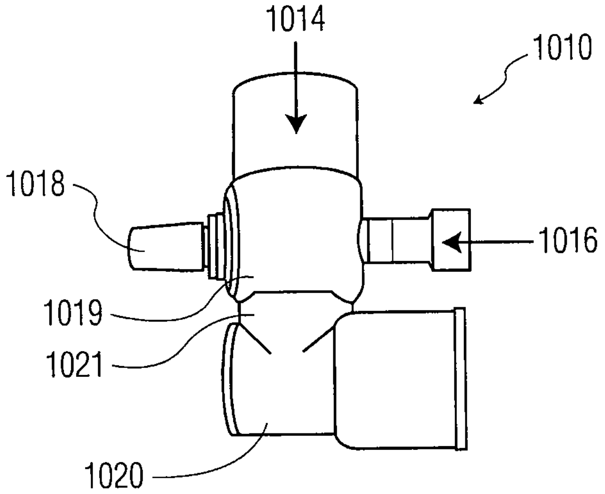
FIG. 10 is a side view of a cross adapter according to another exemplary embodiment of the present invention, for use with the nebulizer of FIG. 6.
Figure 11:
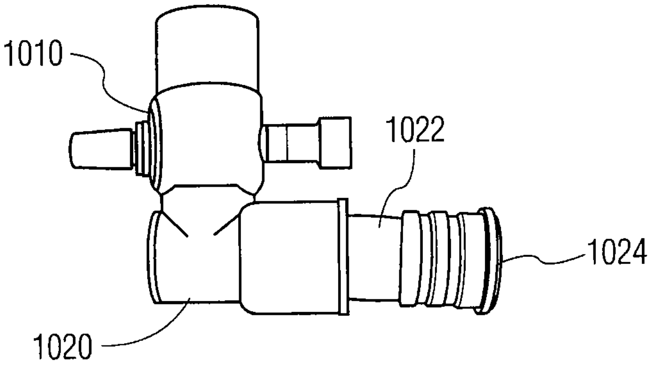
FIG. 11 is a side view of the cross adapter of FIG. 10 with a heat moisture exchanger media partially inserted therein.
Figure 12:
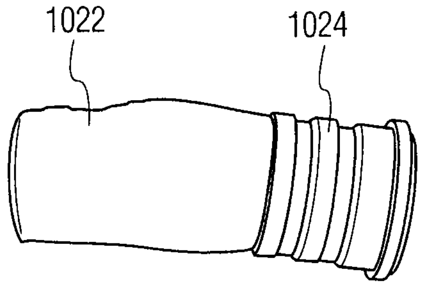
FIG. 12 is a side view of the heat moisture exchanger media used with the cross adapter of FIG. 10.

In an alternative embodiment of a nebulizer system shown in FIGS. 10-12, instead of T-adapter 610, a cross adapter 1010 is used. Cross adapter 1010 includes four ports, including a nebulizer coupling port 1014, an inlet port 1016, and an outlet port 1018, similar to nebulizer coupling port 614, breathing gas inlet 616, and breathing gas outlet 618 disclosed above with respect to T-adapter 610.

Cross adapter 1010 further includes a drain port 1019 that allows condensed medication and/or humidification vapor (in the form of rainout) to drain away from the flow of breathing gas. Drain port 1019 is disposed at a low point in cross-adapter 1010 and is positioned below nebulizer coupling port 1014 in order to allow gravity to drain liquid to a drain collector 1020 that is coupled to drain port 1019. Drain port 1019 includes a slit 1021 that allows liquid to drain away from cross adapter 1010.

A heat moisture exchanger (HME) absorbent media 1022 may be inserted into drain collector 1020, as illustrated in FIGS. 11 and 12, to absorb the condensate that drains into drain port 1019. Exemplary HME-absorbent media 1022 includes a hygroscopic material, such as, for example, Hygrobac S, manufactured by Mallinckrodt of Haxelwood, Mo. or THERMOVENT® HEPA, manufactured by Smiths Medical International of Watford, UK.

Illustrated drain collector 1020 includes a removable cap 1024 that may be removed to replace a used HME-absorbent media 1022 with a fresh HME-absorbent media 1022. Optionally, HME-absorbent media 1022 may be coated or infused with a colorant responsive to fluid present in media 1022 in order to indicate that media 1022 is full of fluid and must be replaced, as well as to ensure the non-reuse of the media 1022. Still optionally, HME-absorbent media 1022 may be coated with an anti-microbial material to reduce the growth of bacteria on/in HME-absorbent media 1022.

Operation of nebulizer system 600 will be discussed with reference to FIGS. 6-9A, as well as flow chart 1300 of FIG. 13. While nebulizer system 600 with adapter 610 is discussed, those skilled in the art will recognize from the description herein that nebulizer system 600 with any alternative adaptor disclosed herein is also applicable.

In STEP 1302, a user (not shown) operates nebulizer 601 to nebulize medication according to the operation of nebulizer 601. In STEP 1304, the nebulized medication is transmitted into mixing chamber 615. Simultaneously with STEPs 1302 and 1304, in STEP 1306, gas, which may be heated and humidified, is transmitted from inlet port 616, across gap 622, and to outlet 618. In STEP 1308, the gas flow draws the nebulized medication into gap 622 to outlet port 618, thereby entraining the nebulized medication into the heated and humidified gas flow.

In STEP 1310, the gas flow with the nebulized medication is transmitted to a breathing device, such as, for example, nasal cannula 606, for inhalation by the patient. Optionally, in STEP 1312, when adapter 1010 is used, nebulized medication that is not drawn into gap 622 may be collected in drain collector 1020. HME-absorbent media 1022 in drain collector 1020 may change color to indicate the presence of fluid in HME-absorbent media 1022, signifying to a user that HME-absorbent media 1022 may be replaced.

Figure 14:
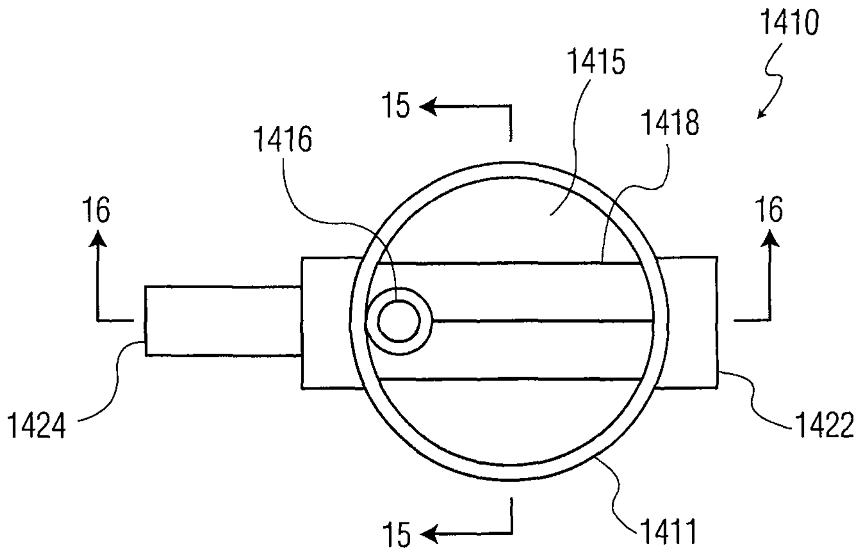
FIG. 14 is a top plan view of an adapter according to another exemplary embodiment of the present invention, for use with the nebulizer of FIG. 6.
Figure 15:
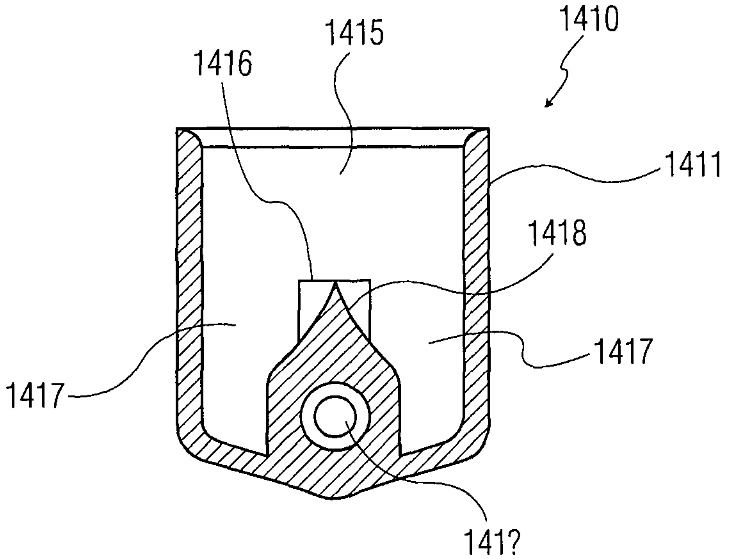
FIG. 15 is a lateral cross-sectional view of the adapter of FIG. 14, taken along lines 15-15 of FIG. 14.
Figure 16:
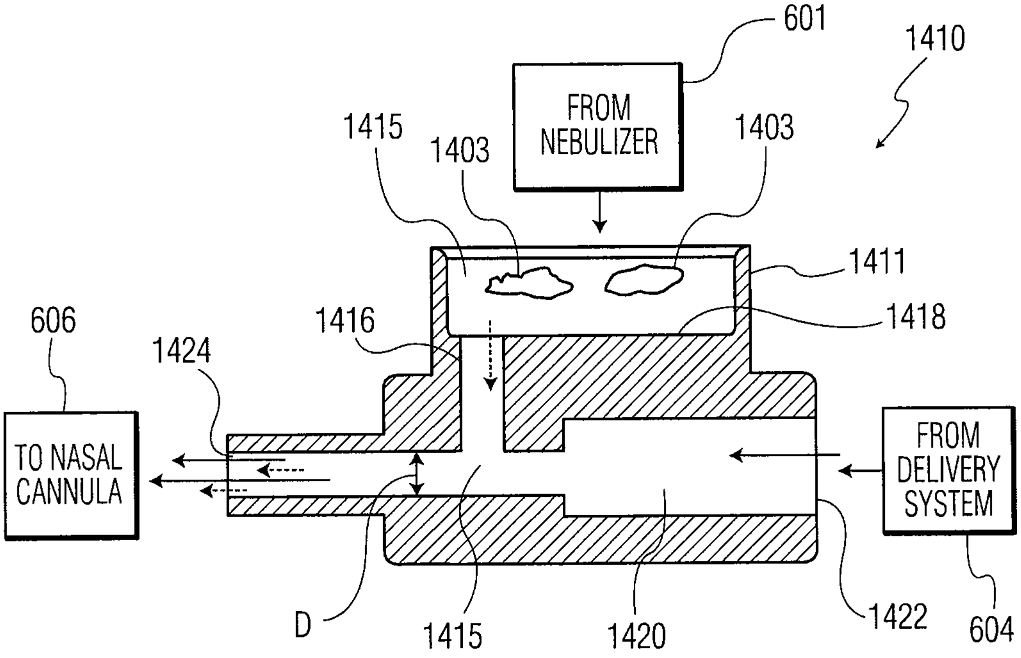
FIG. 16 is a longitudinal cross-sectional view of the adapter of FIG. 14, taken along lines 16-16 of FIG. 14.

In an alternative embodiment of the present invention, illustrated in FIGS. 14-16, an adapter 1410 releasably connects nebulizer 601 to delivery system 604. Adapter 1410 includes a body 1411 that defines an aerosol chamber 1415 into which an aerosol cloud 1403 of medication is directed after being generated by nebulizer 601. Aerosol chamber 1415 includes an opening/passageway 1416 into and through which aerosol cloud 1403 travels to mix with breathing gas from delivery system 604. Aerosolized cloud 1403 is represented by a broken arrow in FIG. 16 as medication flows through passageway 1416 to be entrained with the breathing gas from delivery system 604.

Aerosol chamber 1415 is generally bifurcated into two separate pockets 1417 that are separated by a sloped baffle 1418. Opening/passageway 1416 extends vertically through baffle 1418 and provides fluid communication between aerosol chamber 1415 and a through-passage 1420. Pockets 1417 act as a reservoir for residual condensation from aerosol cloud 1403, as well as from any of the heated and humidified breathing gas that may have traveled upward through opening/passageway 1416 and into chamber 1415. Condensed liquid is retained in pockets 1417 and is not delivered to the patient. In order to drain liquid from pockets 1417, adapted 1410 may be removed from nebulizer 601 and up-ended so that the fluid drains from adapter 1410.

Body 1411 also includes through-passage 1420 that extends through body 1411 from a breathing gas inlet end 1422 that is coupled to delivery system 604 to a breathing gas outlet end 1424 that is coupled to nasal cannula 606. As shown in FIG. 16, breathing gas outlet end 1424 has a diameter "D."

Breathing gas generated by delivery system 604 is represented by solid arrows in through-passage 1420. Passageway 1416 provides fluid communication between aerosol chamber 1415 and through-passage 1420 such that opening/passageway 1416 forms an opening between breathing gas inlet end 1422 and breathing gas outlet end 1424.

The passage of the breathing gas through through-passage 1420 generates a Venturi effect that draws aerosol cloud 1403 through opening/passageway 1416 and into through-passage 1420, where the medication in aerosol cloud 1403 mixes with the breathing gas, as indicated by both the broken arrows (aerosolized medication) and solid arrows (breathing gas) at breathing gas outlet end 1424 of body 1411. Thus, the medication becomes entrained within the breathing gas.

Figure 17:
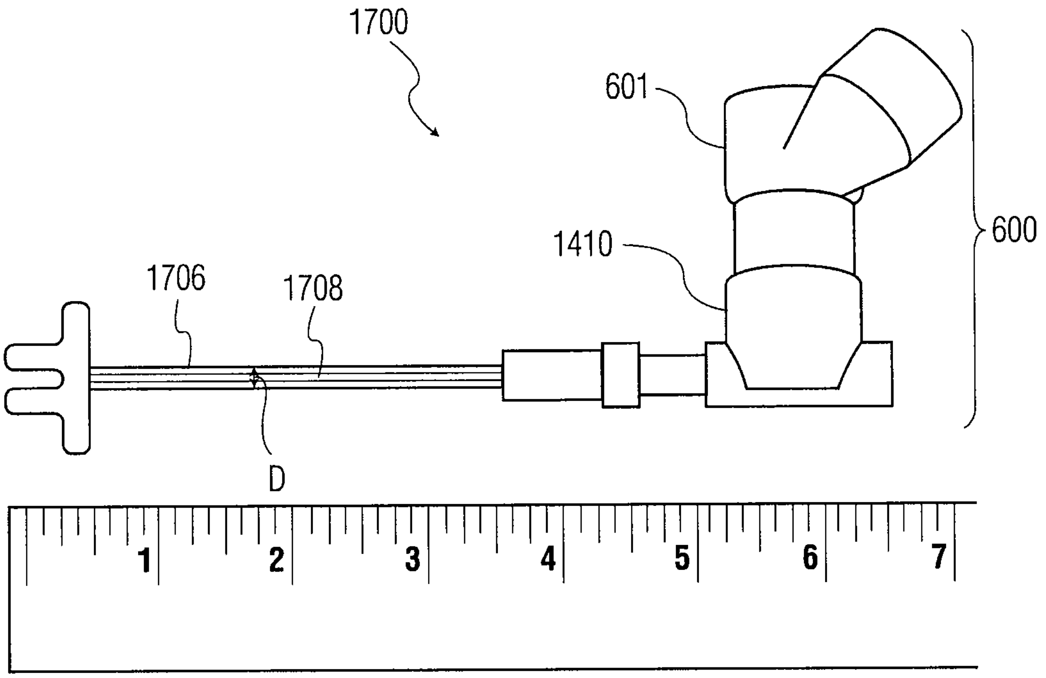
FIG. 17 is a side elevational view of a breathing gas delivery system incorporating an adapter according to an exemplary embodiment of the present invention coupled to the nebulizer assembly of FIG. 7 and also coupled to a nasal cannula.

An exemplary nasal cannula 1706 for use with adapter 1410 is illustrated in FIG. 17. Nasal cannula 1706 is releasably coupled to adapter 1410 to form a breathing gas delivery system 1700. System 1700 may be used to deliver medication from nebulizer 601 to a patient.

For neonatal use, nasal cannula 1706 may have an overall length of about 4½ inches (about 11.4 cm). This length is shorter than prior art neonatal cannulae, which typically have an overall length of about 13 inches (about 33 cm). The shorter length of cannula 1706 provides for delivery of heated and humidified breathing gas and aerosol mist with minimal loss of temperature and resulting condensation. The length of nasal cannula 1706 also allows a caregiver to hold both the patient and system 1700 during treatment of the patient. However, it will be understood by those of ordinary skill in the art that normal length cannulae may also be used for neonatal patients in conjunction with system 1700.

Further, the inner lumen 1708 of cannula 1706 has a diameter "D" that is about the same as the diameter "D" of breathing gas outlet end 1424. The common diameter eliminates any dead spots between breathing gas outlet end 1424 and inner lumen 608 where condensate may form.

Because of the short length of cannula 1706, nebulizer system 600 may need to be held by a caregiver during treatment. For neonatal use, because only a small volume (about 1 to about 6 ml.) of medication is nebulized in nebulizer 601, the duration of treatment is relatively short, and the caregiver can easily hold nebulizer system 600 for the duration of the treatment.

In another alternative embodiment of a nebulizer system shown in FIGS. 18-21, instead of T-adapter 610, an angled adapter 1810 is used. Angled adaptor 1810 includes a body 1811 defining an internal breathing gas mixing chamber 1815. Angled adaptor includes a nebulizer coupling port 1814 that couples angled adapter 1810 to nebulizer 601. Nebulizer coupling port 1814 provides for fluid communication between nebulizer outlet port 1809 and internal breathing gas mixing chamber 1815 such that aerosolized medication may be transmitted from nebulizer 601 to internal breathing gas mixing chamber 1815.

Angled adapter 1810 also includes a breathing gas inlet 1816 and a breathing gas outlet 1818. Outlet 1818 extends outwardly from body 1811 and is adapted to couple to a breathing device, such as nasal cannula 606 (shown in FIG. 7). Inlet 1816 extends from body 1811 and is adapted to couple to gas delivery system 604 (shown in FIG. 7). Inlet 1816 and outlet 1818 are generally co-axial, with an opening, such as opening 1822, separating inlet 1816 from outlet 1818 and communicating with chamber 1815. Opening 1822 may be an oval about 0.2 inches by about 0.1 inches. For example, opening 1822 may be an oval that is 0.202 inches by 0.132 inches.

Figure 18:
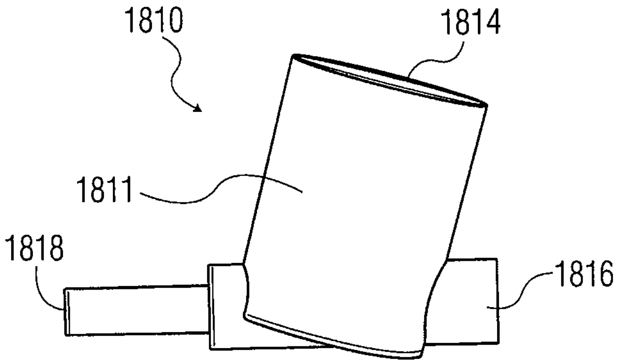
FIG. 18 is a side elevational view of an angled adaptor according to another exemplary embodiment of the present invention, for use with the nebulizer of FIG. 6.
Figure 19:
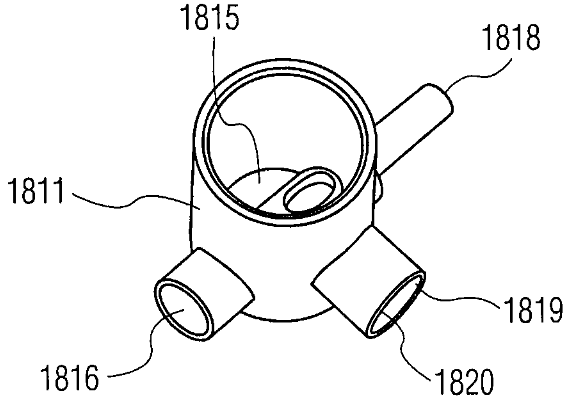
FIG. 19 is a perspective top view of the angled adaptor of FIG. 18
Figure 20:
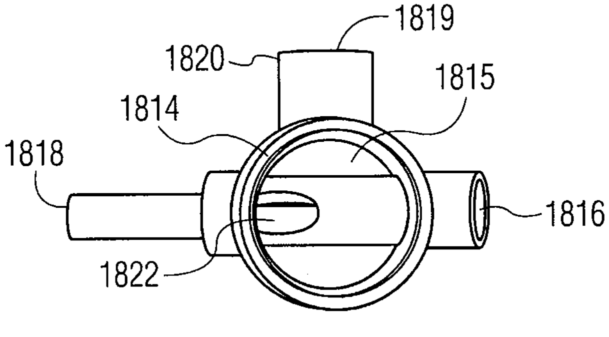
FIG. 20 is an angled top view of the angled adaptor of FIG. 18.
Figure 21:
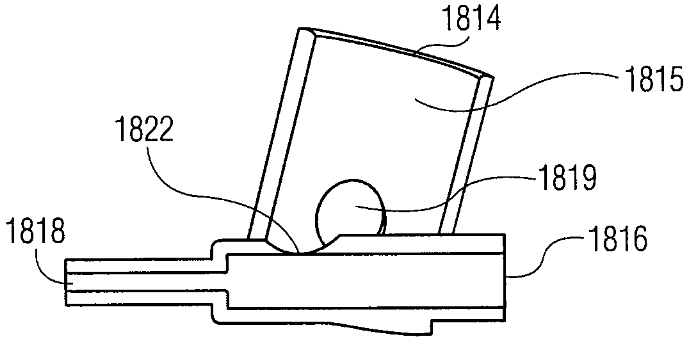
FIG. 21 is a side cross-sectional view of the adaptor of FIG. 18 taken along lines 21-21 of FIG. 20.

As illustrated in FIG. 18, nebulizer coupling port 1814 of angled adaptor 1810 is angled with respect to a line perpendicular to the flow of the breathing gas through adaptor 1810. In an exemplary embodiment, nebulizer coupling port 1814 may form an angle of approximately 15° with respect to a line perpendicular to the flow of gas. Nebulizer coupling port 1814 is angled to deliver a flow of aerosol in the direction of the flow of gas from breathing gas inlet 1816 to breathing gas outlet 1818 (i.e., toward outlet 1818). Angling nebulizer coupling port 1814 may be desirable in order to direct the flow of aerosol directly to the opening where it meets heated/humidified gas flow, thereby improving aerosolization and entrainment of the aerosol w/in the breathing gas flow.

Angled adapter 1810 further includes a pressure-relief port 1819 that allows the relief of pressure away from the flow of breathing gas. Pressure-relief port 1819 is disposed at a side in angled adapter 1810, and is in communication with chamber 1815. Pressure-relief port 1819 may include a hydrophobic membrane 1820. Hydrophobic membrane 1820 prevents build up of pressure within the chambers that may affect the aerosolization ability of the nebulizer. It has been discovered that increased pressure within the chamber 1815 may slow down or inhibit the production of aerosol by the nebulizer. The addition of hydrophobic membrane 1820 allows the venting of excess pressure from within the chamber 1815, thereby allowing the nebulizer 601 to better produce aerosol, while also preventing the aerosol from escaping to atmosphere. Suitable materials for the hydrophobic membrane 1820 will be known to one of ordinary skill in the art from the description herein.

In another alternative embodiment of a nebulizer system shown in FIGS. 22-25, instead of T-adapter 610, an nebulizer cup adapter 2210 is used. Cup adaptor 2210 includes a body 2211 defining an internal breathing gas mixing chamber 2215. Cup adaptor includes a nebulizer coupling port 2214 that couples cup adapter 2210 to nebulizer cup 2201. Nebulizer coupling port 2214 provides for fluid communication between nebulizer outlet port 2209 and internal breathing gas mixing chamber 2215 such that aerosolized medication may be transmitted from nebulizer 2201 to internal breathing gas mixing chamber 2215.

Figure 22:
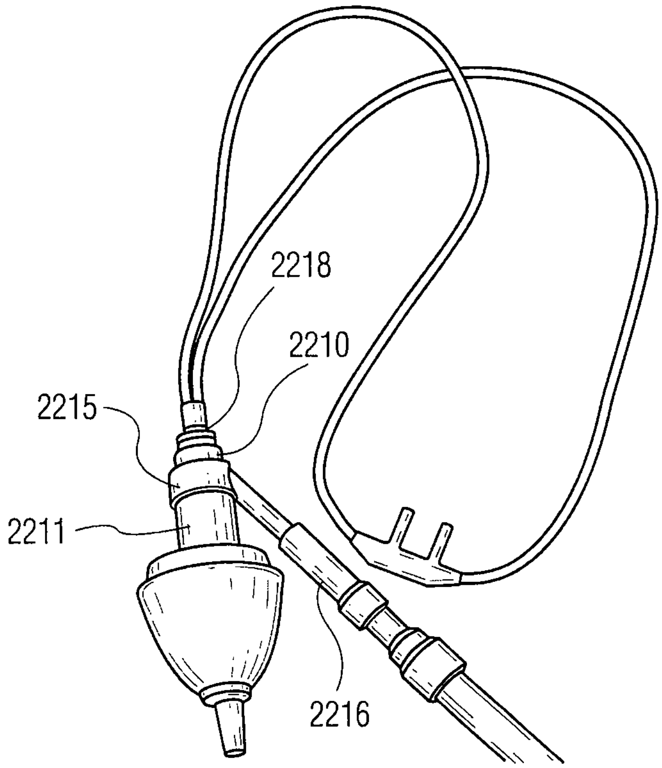
FIG. 22 is a side elevational view of an assembled nebulizer system according to another exemplary embodiment of the present invention.
Figure 23:
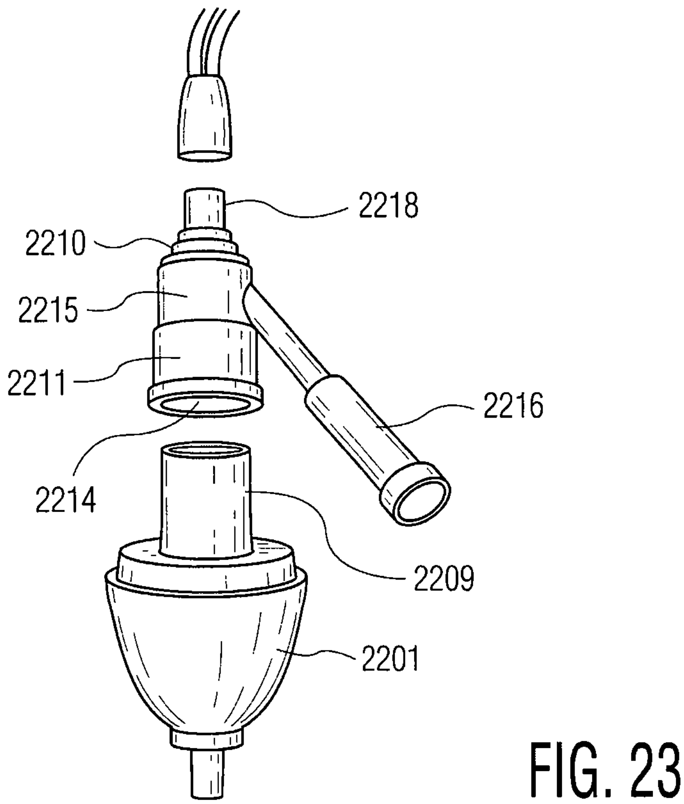
FIG. 23 is a side elevational view of an unassembled nebulizer system of FIG. 22.

Cup adapter 2210 also includes a breathing gas inlet 2216 and a breathing gas outlet 2218. Outlet 2218 extends outwardly from body 2211 and is adapted to couple to a breathing device. Inlet 2216 extends from body 2211 and is adapted to couple to gas delivery system 604 (shown in FIG. 7). Inlet 2216 and outlet 2218 are angled with respect to each other, with an opening separating inlet 2216 from outlet 2218 and communicating with chamber 2215. As illustrated in FIG. 22, nebulizer coupling port 2214 of cup adaptor 2210 is coaxial with respect to outlet 2218.

Figure 24:
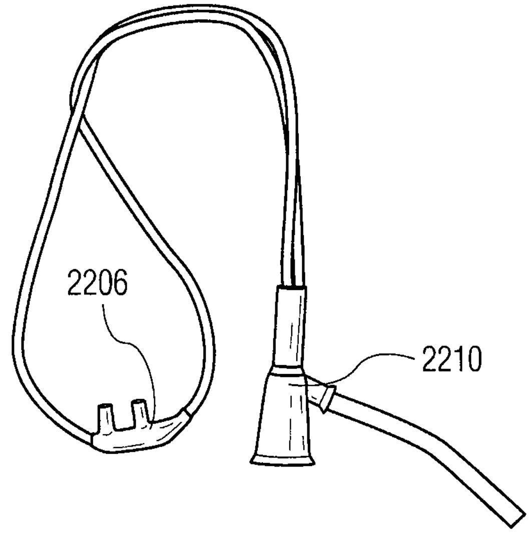
FIG. 24 is a side elevational view of the nebulizer system of FIG. 22 with a cannula.
Figure 25:
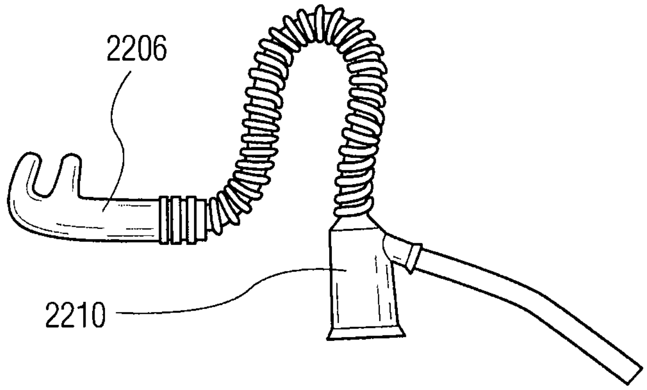
FIG. 25 is a side elevational view of the nebulizer system of FIG. 22 with another cannula.

As illustrated in FIGS. 24 and 25, outlet 2218 of cup adaptor 2210 may be adapted to be coupled to a nasal cannula 2206. Nasal cannula 2206 may be a low diameter nasal cannula (as shown in FIG. 24) or a high diameter nasal cannula (as shown in FIG. 25). Suitable cannulas, and other breathing devices for coupling to outlet 2218 of cup adaptor 2210, will be known to one of ordinary skill in the art from the description herein.

Figure 26:
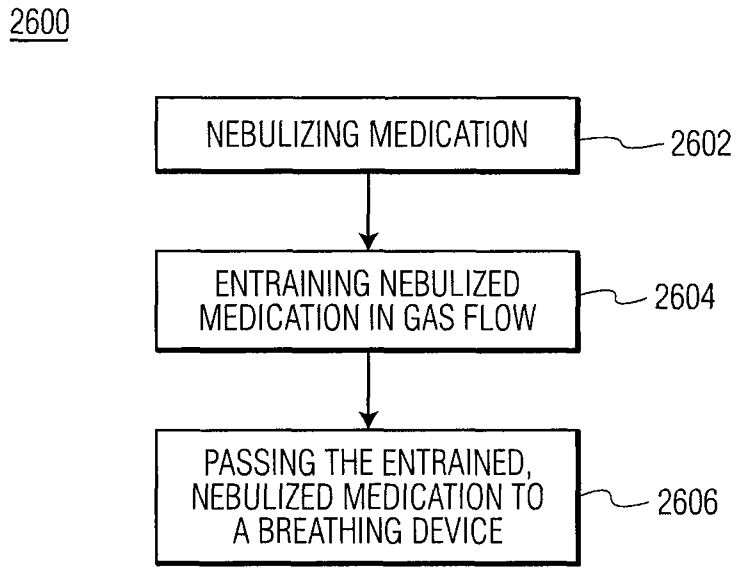
FIG. 26 is a flow chart illustrating operation of the nebulizer system of FIG. 22.

Operation of the above alternative embodiment of the nebulizer system will be discussed with reference to FIGS. 22-25, as well as flow chart 2600, illustrated in FIG. 26. While the nebulizer system with nebulizer cup adapter 2210 is discussed, those skilled in the art will recognize from the description herein that any alternative adaptor disclosed herein is also applicable.

In STEP 2602, a user (not shown) operates nebulizer cup 2201 to nebulize medication according to the operation of nebulizer 2201. Operation of nebulizer cup 2201 to nebulize medication will be understood by one of ordinary skill in the art from the description herein.

In STEP 2604, the nebulized medication is entrained in a gas flow. In an exemplary embodiment, a flow of gas, which may be heated and humidified, is transmitted through cup adaptor 2210 from inlet 2216 to outlet 2218. The nebulized medication from nebulizer 2201 is entrained in the gas flow. For example, the gas flow may draw the nebulized medication into the flow via the opening between inlet 2216 and outlet 2218, i.e., due to a Venturi effect. For another example, the nebulized medication may be forced into the gas flow due to an air pressure difference between the nebulizer outlet port 2209 and the adaptor gas outlet 2218.

In STEP 2606, the entrained nebulized medication is passed to a breathing device. In an exemplary embodiment, the entrained nebulized medication is passed to a nasal cannula 2206. Suitable cannulas will be known to one of ordinary skill in the art from the description herein.

It will be understood by one of ordinary skill in the art that the above operation of the nebulizer system may include any of the additional steps set forth with respect to nebulizer system 600.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A nebulizer assembly comprising:

a reservoir for containing a liquid;

a nebulizer for producing an aerosolized gas using the liquid;

an aerosolized gas outlet coupled to the nebulizer to pass the aerosolized gas, the aerosolized gas outlet in fluid communication with a flow of a breathing gas at a junction;

a breathing gas conduit having an inlet end and an outlet end in fluid communication with the junction;

a manifold; and a heating chamber disposed around an exterior of the reservoir, wherein the heating chamber includes a heating fluid inlet in fluid communication with the heating chamber for providing heating fluid to the heating chamber and a heating fluid outlet in fluid communication with the heating chamber for discharging the heating fluid from the heating chamber, the heating chamber maintaining the heating fluid separate from the liquid contained by the reservoir, wherein the inlet end of the breathing gas conduit, the heating fluid inlet, and the heating fluid outlet are coupled to the manifold.

2. A method of heating a medication to be nebulized and providing the nebulized medication to a patient for inhalation, the method comprising the steps of:

generating a heated and humidified breathing gas;

transmitting the heated and humidified breathing gas through a first lumen in a delivery tube;

insulating the heated and humidified breathing gas with a fluid flowing through a second lumen in the delivery tube;

discharging the heated and humidified breathing gas from the delivery tube to a chamber;

providing a medication in a nebulizer reservoir;

transmitting the fluid from the second lumen to a heating cavity surrounding the nebulizer reservoir; thereby heating the medication in the nebulizer reservoir with the fluid;

nebulizing the medication in the nebulizer reservoir;

combining the nebulized medication with the heated and humidified breathing gas in the chamber; and transmitting the combined nebulized medication and heated and humidified breathing gas to a patient for inhalation.

3. The method according to claim 2, further comprising the step of flowing the fluid from the heating cavity to a third lumen in the delivery tube.

4. A nebulizer system comprising:

a nebulizer for generating an aerosol mist of a medication, wherein the nebulizer is configured to deliver the aerosol mist via a nebulizer outlet port; and a breathing gas mixing chamber separate from the nebulizer and coupled to the nebulizer outlet port in order to receive the aerosol mist generated by the nebulizer via the nebulizer outlet port, wherein the breathing gas mixing chamber comprises:

a nebulizer coupling port for coupling the breathing gas mixing chamber to the nebulizer outlet port;

a breathing gas inlet adapted to couple to a gas delivery system;

a breathing gas outlet adapted to couple to a breathing device; and an opening between the breathing gas inlet and the breathing gas outlet, the opening being in fluid communication with the nebulizer outlet port.

5. The nebulizer system according to claim 4, wherein the breathing gas chamber further comprises a drain port, and further comprising:

a drain collector coupled to the drain port.

6. The nebulizer system according to claim 5, wherein the drain collector includes a heat moisture exchanger-absorbent media disposed therein.

7. The nebulizer system according to claim 6, wherein the media changes color responsive to a fluid present in the media.

8. The nebulizer system according to claim 6, wherein the media comprises an anti-microbial material.

9. The nebulizer system according to claim 4, wherein the breathing gas mixing chamber further comprises a through-passage extending from the breathing gas inlet to the breathing gas outlet, the through-passage including the opening.

10. The nebulizer system according to claim 4, wherein the opening comprises a gap.

11. The nebulizer system according to claim 10, wherein the gap is less than about 5 millimeters.

12. The nebulizer system according to claim 4, further comprising a nasal cannula coupled to the breathing gas outlet port.

13. The nebulizer system according to claim 12, wherein the nasal cannula has an overall length of about 4½ inches for neonatal use.

14. A method of adding a medication to a gas flow comprising the steps of:

a) nebulizing the medication with a nebulizer;

b) delivering the nebulized medication from the nebulizer via a nebulizer outlet port;

c) receiving the nebulized medication through a nebulizer coupling port of a breathing gas mixing chamber, the breathing gas mixing chamber separate from the nebulizer, the nebulizer coupling port coupled to the nebulizer outlet port;

d) receiving the gas flow through a breathing gas inlet of the breathing gas mixing chamber; and e) entraining the nebulized medication into the gas flow.

15. The method according to claim 14, further comprising the step of passing the entrained, nebulized medication to a nasal cannula.

16. The method according to claim 14, wherein step (b) comprises:

b1) transmitting the nebulized medication to a breathing gas mixing chamber; and b2) transmitting the gas flow from an inlet to an outlet within the chamber, the chamber including an opening between the inlet and the outlet, wherein the gas flow draws the nebulized medication into the opening for mixing with the gas flow and passage to the outlet.

17. The method according to claim 16, further comprising the step of transmitting the gas flow with the nebulized medication to a breathing device for inhalation by a patient.

18. The method according to claim 16, further comprising the step of collecting nebulized medication not drawn into the gap in a drain collector.

19. The method according to claim 16, wherein transmitting the gas flow comprises transmitting a heated and humidified gas flow.

20. A nebulizer adaptor for entraining a nebulized medication into a breathing gas, the nebulizer adaptor comprising:

a mixing chamber;

a nebulizer coupling port adapted to be coupled to a nebulizer outlet port and to deliver the nebulized medication from the nebulizer outlet port to the mixing chamber;

a breathing gas inlet adapted to couple to a gas delivery system;

a breathing gas outlet adapted to couple to a breathing device, the breathing gas inlet and breathing gas outlet defining a breathing gas flow path separate from the mixing chamber; and an opening in the breathing gas flow path between the breathing gas inlet and the breathing gas outlet, the opening being in fluid communication with the mixing chamber.

* * * * *